(12) United States Patent
Xie et al.

(10) Patent No.: US 11,335,466 B2
(45) Date of Patent: May 17, 2022

(54) METHOD FOR DETERMINING DISEASE SYMPTOM RELATIONS USING ACCEPTANCE AND REJECTION OF RANDOM SAMPLES

(71) Applicant: TENCENT AMERICA LLC, Palo Alto, CA (US)

(72) Inventors: Yusheng Xie, Mountain View, CA (US); Tao Yang, Mountain View, CA (US); Min Tu, Cupertino, CA (US); Nan Du, Santa Clara, CA (US); Shih-Yao Lin, Palo Alto, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 216 days.

(21) Appl. No.: 16/277,430

(22) Filed: Feb. 15, 2019

(65) Prior Publication Data
US 2020/0265959 A1   Aug. 20, 2020

(51) Int. Cl.
*G16H 50/70* (2018.01)
*G16H 10/60* (2018.01)
*G06N 7/00* (2006.01)

(52) U.S. Cl.
CPC ............. *G16H 50/70* (2018.01); *G06N 7/005* (2013.01); *G16H 10/60* (2018.01)

(58) Field of Classification Search
CPC ......... G16H 50/70; G16H 10/60; G06N 7/005
USPC .......................................................... 705/3
See application file for complete search history.

(56) References Cited

U.S. PATENT DOCUMENTS

| | | | | |
|---|---|---|---|---|
| 7,814,035 B2* | 10/2010 | Mundie | ............... | G06F 16/2465 706/20 |
| 8,744,557 B2* | 6/2014 | Sternickel | ............ | A61B 5/7253 600/509 |
| 11,170,484 B2* | 11/2021 | Hanina | ................. | H04N 7/188 |
| 11,200,967 B1* | 12/2021 | Jain | ........................ | G16H 50/70 |
| 2003/0065535 A1* | 4/2003 | Karlov | .................. | G16H 15/00 705/2 |
| 2004/0034465 A1* | 2/2004 | Spiesberger | .............. | G01S 5/02 702/150 |
| 2004/0243328 A1* | 12/2004 | Rapp | ..................... | A61B 5/7264 702/71 |
| 2013/0325769 A1* | 12/2013 | Downs | ................... | G06N 7/005 706/18 |
| 2020/0265959 A1* | 8/2020 | Xie | ........................ | G16H 50/20 |

OTHER PUBLICATIONS

Nguyen, Vu, et al. "Regret for expected improvement over the best-observed value and stopping condition." Asian Conference on Machine Learning. (Year: 2017).*

(Continued)

*Primary Examiner* — Michael Tomaszewski
*Assistant Examiner* — Rachael Sojin Stone
(74) *Attorney, Agent, or Firm* — Sughrue Mion, PLLC

(57) ABSTRACT

A method and apparatus are provided that includes iteratively sampling candidates from medical records and evaluating whether ones of the candidates better explain a member from the medical records. The iterations replace the member with the candidates and depending on whether the candidates better explain the member from the medical records may be weighted in a next iteration.

20 Claims, 4 Drawing Sheets

(56) References Cited

OTHER PUBLICATIONS

Nguyen et al., "Regret for Expected Improvement over the Best-Observed Value and Stopping Condition", Proceedings of Machine Learning Research, 2017, vol. 77, retrieved from Internet <URL: http://proceedings.mlr.press/v77/nguyen17a/nguyen17a.pdf>, pp. 279-294 (total 16 pages).
International Search Report and Written Opinion of the International Searching Authority for PCT/US2020/017671 dated May 13, 2020.

\* cited by examiner

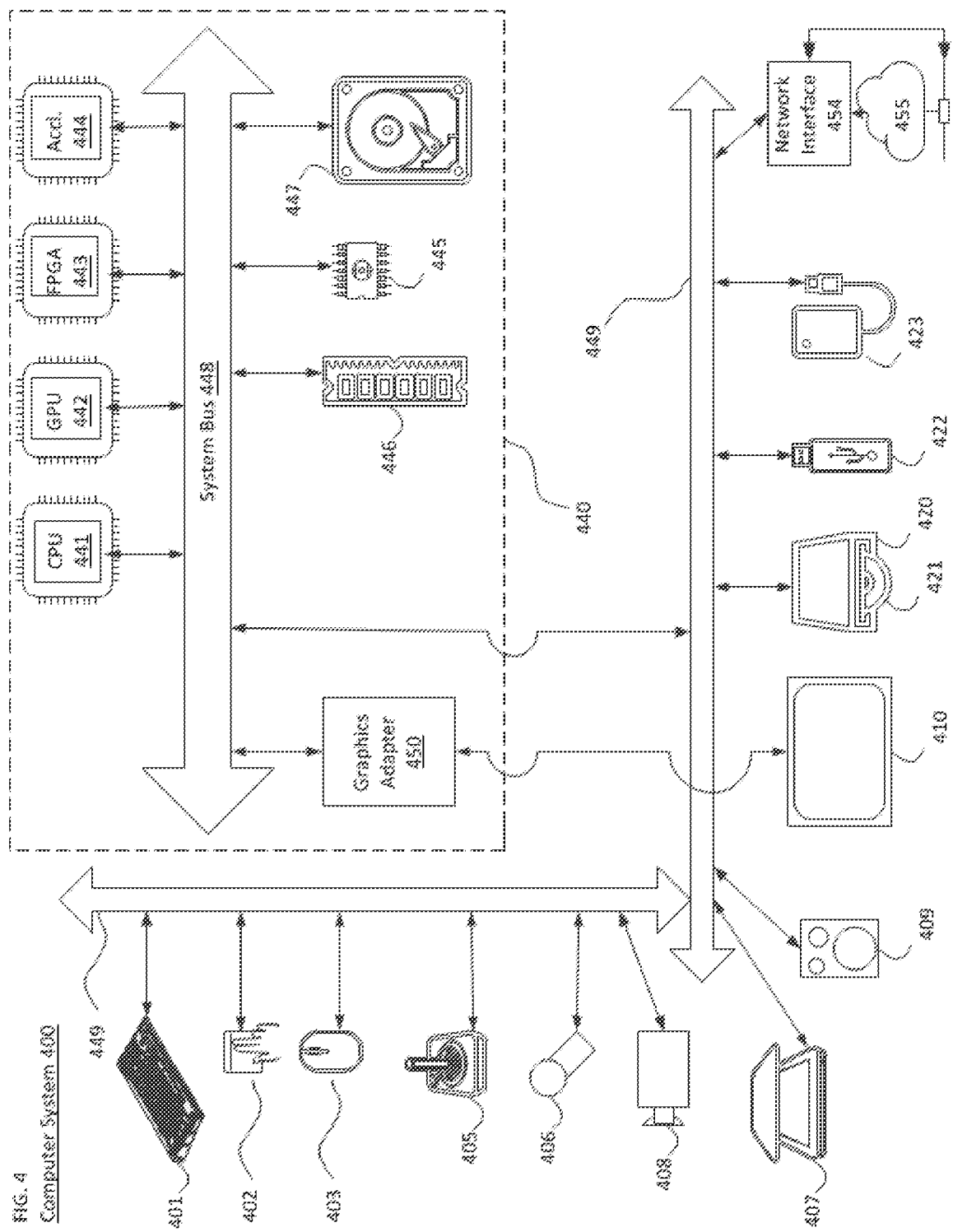

METHOD FOR DETERMINING DISEASE SYMPTOM RELATIONS USING ACCEPTANCE AND REJECTION OF RANDOM SAMPLES

BACKGROUND

1. Field

The disclosed subject matter relates to a novel sampling algorithm that is useful in learning probabilistic relationships between symptoms and diseases from a large amount of electronic health records.

2. Description of Related Art

The healthcare sector generates a large amount of records concerning patients' symptoms and diagnosed diseases. It is a common challenge to conclude useful, concise knowledge from the vast number of such records. One approach is to use a bipartite Bayesian network that models the causal relations between symptoms and diseases. Under this Bayesian framework, the aforementioned challenge becomes learning networks weights from symptom-diagnosis records.

Techniques, in a Bayesian bipartite network framework for example, are therefore needed to learn the probabilities of symptoms, given a diagnosed disease, from symptom-disease diagnosis records.

In certain computer environments, implementation of learning Bayesian probabilities, such as in symptom-disease relationships, have technical problems such as prohibitive adaptability and latency by use of No-U-Turn Sampling (NUTS) or Markov Chain Monte Carlo (MCMC) methods.

Therefore, technical solutions are desired to avoid such less adaptive and slower implementations.

SUMMARY

In view of previous attempts at predicting symptom-disease Bayesian probabilities, where such attempts mainly focus on binary predictions, the disclosed subject matter herein is instead a novel discriminative treatment of learnable probabilities including dynamically deciding to accept or reject a sample.

In exemplary embodiments, there is an apparatus comprising at least one memory configured to store computer program code and at least one hardware processor configured to access the computer code and operate as instructed by the computer program code. The computer program code includes obtaining code configured to cause the at least one hardware processor to obtain medical records. The computer program code further includes sampling code configured to cause the at least one hardware processor to iteratively sample ones of candidates from a matrix of probabilistic interactions among symptoms and diseases that are both indicated by the medical records. The computer program code further includes evaluating code configured to cause the at least one hardware processor to evaluate whether a first candidate of the symptoms and diseases is more likely, than a member of the matrix, in a prior distribution of the first candidate under a set of Bayesian probabilities and with respect to a first subset of the medical records, the first subset comprising all of the medical records that indicate a first of the diseases. The computer program code further includes replacing code configured to cause the at least one hardware processor to, in response to determining that the first candidate is more likely, than a member of the matrix, in the prior distribution of the first candidate under the set of Bayesian probabilities and with respect to the first subset of the medical records, replace the member of the matrix with the first candidate and starting a next iteration, and in response to determining that the first candidate is not more likely, than a member of the matrix, in the prior distribution of the first candidate under the set of Bayesian probabilities and with respect to the first subset of the medical records, replace the member with the first candidate and starting the next iteration with a different weighting.

In exemplary embodiments, the at least one hardware processor is further configured to, before evaluating whether the first candidate of the symptoms and diseases is more likely than the member of the matrix, implement generating a random variable comprising a truncated normal distribution centered at the member of the matrix from one of previous iterations and drawing the first candidate from the random variable.

In exemplary embodiments, the variance of the random variable is adaptively changed based on the previous iterations, and the matrix comprises an n-by-m matrix where n represents the number of symptoms and m represents the number of diseases. Further, at least a plurality of the symptoms overlap between the first subset of the medical records and a second subset of the medical records, the second subset comprising all of the medical records that indicate a second of the diseases.

In exemplary embodiments, the at least one hardware processor is further configured to, in the next iteration, implement evaluating whether a second candidate of the symptoms and diseases is more likely, than the member of the matrix, in a prior distribution of the second candidate under the set of Bayesian probabilities and with respect to the first subset of the medical records, in response to determining that the second candidate is more likely, than the member of the matrix, in the prior distribution of the second candidate under the set of Bayesian probabilities and with respect to the first subset of the medical records, replacing the member of the matrix with the second candidate and starting a second next iteration, and in response to determining that the second candidate is not more likely, than the member of the matrix, in the prior distribution of the second candidate under the set of Bayesian probabilities and with respect to the first subset of the medical records, replacing the member with the second candidate and starting the second next iteration with a second different weighting.

In exemplary embodiments, the at least one hardware processor is further configured to, before the second next iteration, implement determining a first probability density function for each of a plurality of members of the matrix before the member is replaced with the first candidate, determining a second probability density function for each of the plurality of members of the matrix after the member is replaced with the first candidate, determining a first amount of change between the first probability density function and the second probability density function, determining a third probability density function for each of the plurality of members of the matrix after the member is replaced with the second candidate, determining a second amount of change between the first probability density function and the third probability density function, and preventing the second next iteration in response to determining that a difference between the first amount of change and the second amount of change is less than a predetermined threshold.

In exemplary embodiments, the at least one hardware processor is further configured to implement determining the first amount of change and the second amount of change by measuring Kullback-Leibler (KL) divergence.

In exemplary embodiments, wherein the at least one hardware processor is further configured to, before determining the difference and before any one of the next iteration and the another subsequent iteration, implement determining whether a user instruction has been received to halt iteratively sampling the ones of the candidates, and preventing the one of the next iteration and the second next iteration in response to determining that the user instruction has been received.

10. In exemplary embodiments, the at least one hardware processor is further configured to, before any one of the next iteration and the second next iteration, implement determining whether a user instruction has been received to halt iteratively sampling the ones of the candidates, and preventing the one of the next iteration and the second next iteration in response to determining that the user instruction has been received.

BRIEF DESCRIPTION OF THE DRAWINGS

Further features, nature, and various advantages of the disclosed subject matter will be more apparent from the following detailed description and the accompanying drawings in which:

FIG. 4 is a schematic illustration of a simplified block diagram of a system in accordance with an embodiment.

DETAILED DESCRIPTION

Figure 1:
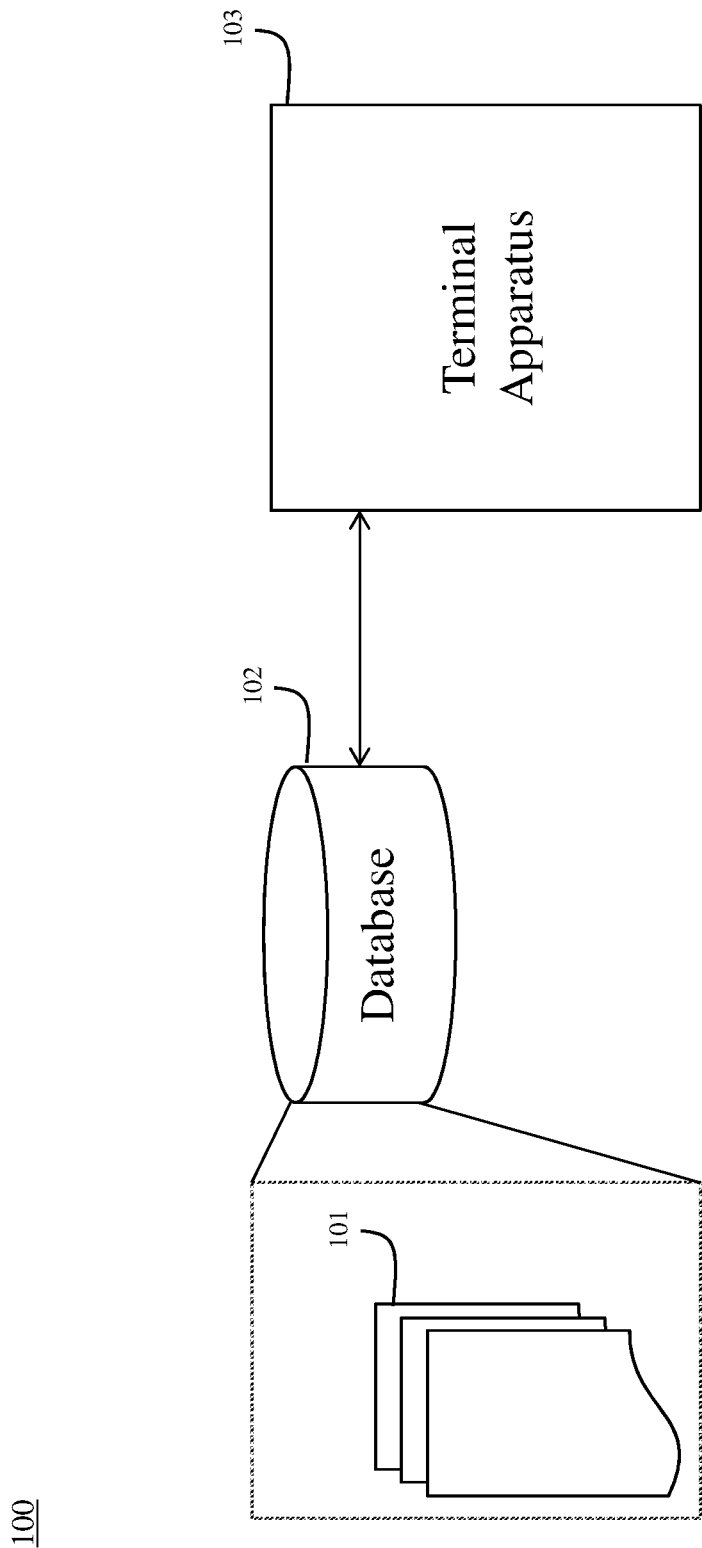
FIG. 1 is a schematic illustration of a simplified block diagram of a system in accordance with an embodiment.

FIG. 1 illustrates a simplified block diagram of a communication system 100 according to an embodiment of the present disclosure. The system 100 includes a database 102 storing include various medical data 101 such as symptoms and diagnoses from multiple patients. That database 102 may be connected to a terminal apparatus 103 via a network (local or global, for example), or the database 102 may be incorporated into the terminal apparatus 103. Details of the terminal apparatus 103 are described further below with respect to FIG. 4.

Medical data 101 may be added to the database 102 in various circumstances, such as when new diagnostic data is created at the terminal apparatus 103. The terminal apparatus 103 may further analyze the medical data 101 as discussed with respect to FIG. 2. According to exemplary embodiments, the terminal apparatus 103 may be a server which distributes results of considering the medical data 101 to other terminal apparatuses.

Figure 2:
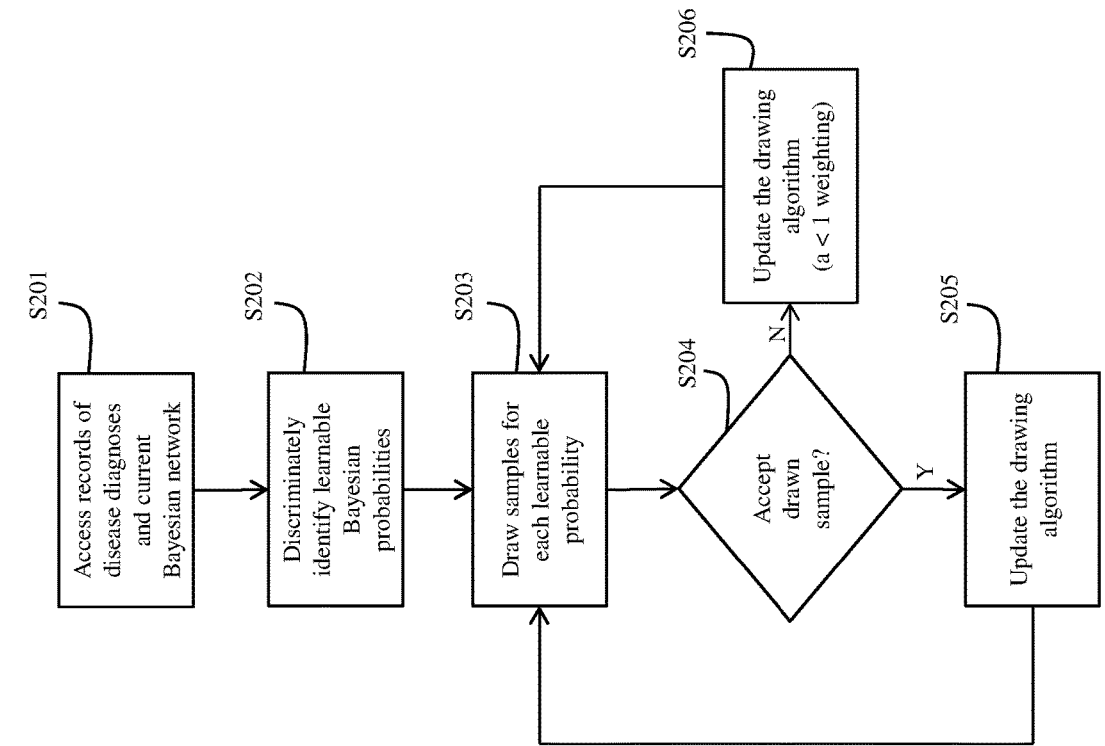
FIG. 2 is a schematic illustration of a simplified flow chart of a communication system in accordance with an embodiment.

FIG. 2 illustrates a flowchart 200 by which the above-described technical problems may be improved upon. At S201, the terminal apparatus 103 accesses records of disease diagnoses and a current Bayesian network. For example, in such network it may be considered that $Q$ is an n-by-m matrix representing probabilistic interactions among n symptoms and m diseases (or diagnoses of diseases).

According to exemplary embodiments and because of the probabilistic nature, it may be considered that $0 \leq Q(i, j) < 1$ for all applicable data i, j. In addition, as there may be many diagnosis records, from medical data 101, each of which associates a disease with a list of symptoms: $L=\{(d_1, s_{1,1}, s_{1,2}, \ldots), (d_2, s_{2,1}, s_{2,2}, \ldots), \ldots\}$. Each $d_i \in \{1, 2, \ldots, m\}$ and $s_{i,j} \in \{1, 2, \ldots, n\}$, which may re-appear and overlap as a number of the diagnosis records, may exceed mn.

At S202, the terminal apparatus 103 discriminately identifies learnable Bayesian probabilities. For example, it is considered that $Q_{>0,1}=\{(i, j)|q(i, j)>0\}$ and $Q_{>0,2}$ may be a set of every $(s_{i,j}, d_i)$ pair appearing in at least one record in L, and $Q_{>0}$ may be a union of $Q_{>0,1}$ and $Q_{>0,2}$, where $Q_{>0}$ represents learnable Bayesian probabilities and where $Q_{>0,1}$ and $Q_{>0,2}$ may define how to discriminate those probabilities.

Such discrimination of those probabilities may be by being reluctant to upgrade an unlikely probability and by being lenient with upgrading or downgrading a likely probability according to exemplary embodiments.

At S203, there is a sampling process in which the terminal apparatus 103 draws samples for each learnable probability for each member of $Q(i, j) \in Q_{>0}$. At each iteration in FIG. 2, there is a proposed random variable (rv) for each member $Q(i, j) \in Q_{>0}$. The rv may be typically a truncated (between 0 and 1) normal distribution and centered at $Q(i, j)$ from a previous iteration, and its variance may adaptively change based on statistics from past iterations.

A sample $p_{ij}$ may be drawn from this rv as a candidate to replace the current $Q(i, j)$ in the $Q$ matrix. In evaluating $p_{ij}$ as a candidate, there is consideration of a collection of diagnosis records $L_j$ which is a subset of the list of symptoms L at S204 as to whether to accept that sample $p_{ij}$.

For example, $L_j$ may contain all records concerning disease $d_j$, and if a newly sampled $p_{ij}$, along with the rest of $Q$ can better explain $L_j$ (such as discussed below), then, at S205, $Q(i, j)=p_{ij}$.

Alternately, if the newly sampled $p_{ij}$, along with the rest of $Q$ does not better explain $L_j$, then, at S206, $Q(i, j)=p_{ij}$ and with an a <1 probability weighting.

As an exemplary embodiment of determining if the newly sampled $p_{ij}$, along with the rest of $Q$ does not better explain $L_j$, it may be considered whether the observed diagnosis records, from the medical data 101, are more probable or likely under a particular set of Bayesian probabilities, and it may also be considered how likely a sampled probability may be in its own prior distribution. Further, a discrimination between $Q_{>0,1}$ and $Q_{>0,2}$ may work by prioritizing $Q_{>0,1}$ over $Q_{>0,2}$.

When, after multiple processes of determining acceptance or rejection for each member of $Q(i, j) \in Q_{>0}$, one sample iteration is completed, a next sample iteration may begin, and as such, there may be iterative processing of determining acceptance or rejection.

Figure 3:
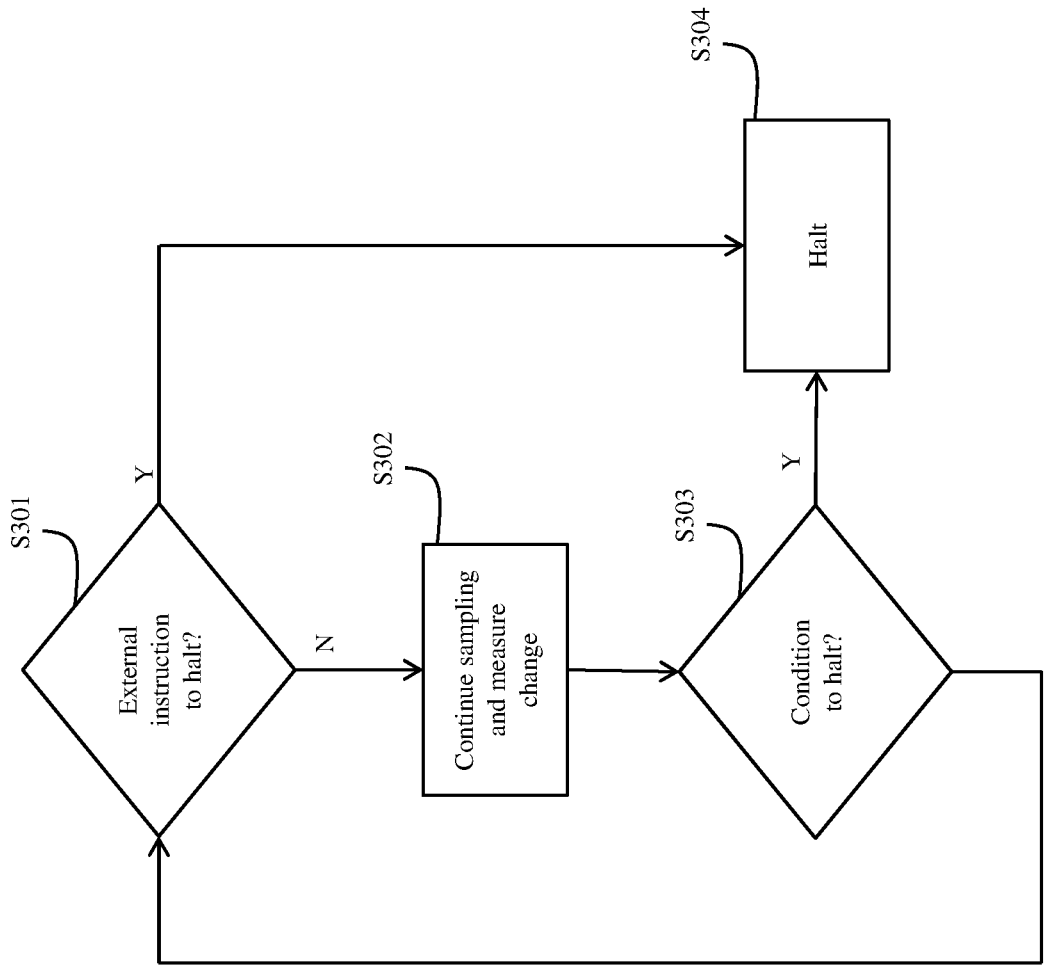
FIG. 3 is a schematic illustration of a simplified flow chart of a communication system in accordance with an embodiment.

FIG. 3 illustrates a flowchart 300 by which the sampling iterations may be halted. For example, at S301 it may be considered whether there is an external instruction to the terminal apparatus 103 to halt the iterations, such as when a practitioner may deem that there are enough samples. If so, then at S304, the iterative sampling may be halted.

Alternately, if at S301 there is not an external instruction to halt, the iterative sampling may continue at S302 with consideration of various metrics, such as an amount of change in overall sample distributions (probability density functions (PDF) for example) of $Q(i, j)$ due to newly sampled one or more $p_{ij}$ values.

At S303, it may be considered, while continuing sampling and accepting new $p_{ij}$ values, whether the overall PDF of $Q(i, j)$ stays about the same or is less than a predetermined threshold, and if so, it may be determined at S303 to halt the iterative sampling. According to exemplary embodiments, changes in PDF maybe measured by Kullback-Leibler (KL) divergence, for example.

According to the features of FIGS. 2 and 3, the embodiments of the present application may accept or reject samples based on the above-described dynamic decisions, and such embodiments thereby improve upon technology in the field by presenting more effective and more adaptive strategies for evidence based diagnosis along with increased capabilities and accuracy as compared to slower NUTS or MCMC methods. For example, at each step in FIGS. 2 and 3, visualizations may be provided indicating KL divergence between a current PDF and a previous step PDF, and in a chart including divergence compared per such steps, divergence may ideally decrease to zero as the steps increase. Additionally, a visualization of the network may be provided including all of Q(i,j) values of which some edges therein will be added, removed and/or strengthened.

Such features may be incorporated with Quick Medical Reference (QMR) networks, Bayesian networks, Noisy-OR networks, MCMC sampling schemes, Gibbs sampling schemes and Metropolis-Hastings sampling schemes according to exemplary embodiments. For QMR networks, the National Institutes of Health U.S. National Library of Medicine provides online descriptions with reference to a Unified Medical Language System (UMLS).

The techniques described below, can be implemented as computer software using computer-readable instructions and physically stored in one or more computer-readable media. For example, FIG. 4 shows a computer system 400 suitable for implementing certain embodiments of the disclosed subject matter.

The computer software can be coded using any suitable machine code or computer language, that may be subject to assembly, compilation, linking, or like mechanisms to create code comprising instructions that can be executed directly, or through interpretation, micro-code execution, and the like, by computer central processing units (CPUs), Graphics Processing Units (GPUs), and the like.

The instructions can be executed on various types of computers or components thereof, including, for example, personal computers, tablet computers, servers, smartphones, gaming devices, internet of things devices, and the like.

The components shown in FIG. 4 for computer system 400 are exemplary in nature and are not intended to suggest any limitation as to the scope of use or functionality of the computer software implementing embodiments of the present disclosure. Neither should the configuration of components be interpreted as having any dependency or requirement relating to any one or combination of components illustrated in the exemplary embodiment of a computer system 400.

Computer system 400 may include certain human interface input devices. Such a human interface input device may be responsive to input by one or more human users through, for example, tactile input (such as: keystrokes, swipes, data glove movements), audio input (such as: voice, clapping), visual input (such as: gestures), olfactory input (not depicted). The human interface devices can also be used to capture certain media not necessarily directly related to conscious input by a human, such as audio (such as: speech, music, ambient sound), images (such as: scanned images, photographic images obtain from a still image camera), video (such as two-dimensional video, three-dimensional video including stereoscopic video).

Input human interface devices may include one or more of (only one of each depicted): keyboard 401, mouse 402, trackpad 403, touch screen 410, joystick 405, microphone 406, scanner 407, camera 408.

Computer system 400 may also include certain human interface output devices. Such human interface output devices may be stimulating the senses of one or more human users through, for example, tactile output, sound, light, and smell/taste. Such human interface output devices may include tactile output devices (for example tactile feedback by the touch-screen 410, or joystick 405, but there can also be tactile feedback devices that do not serve as input devices), audio output devices (such as: speakers 409, headphones (not depicted)), visual output devices (such as screens 410 to include CRT screens, LCD screens, plasma screens, OLED screens, each with or without touch-screen input capability, each with or without tactile feedback capability—some of which may be capable to output two dimensional visual output or more than three dimensional output through means such as stereographic output; virtual-reality glasses (not depicted), holographic displays and smoke tanks (not depicted)), and printers (not depicted).

Computer system 400 can also include human accessible storage devices and their associated media such as optical media including CD/DVD ROM/RW 420 with CD/DVD or the like media 421, thumb-drive 422, removable hard drive or solid state drive 423, legacy magnetic media such as tape and floppy disc (not depicted), specialized ROM/ASIC/PLD based devices such as security dongles (not depicted), and the like.

Those skilled in the art should also understand that term "computer readable media" as used in connection with the presently disclosed subject matter does not encompass transmission media, carrier waves, or other transitory signals.

Computer system 400 can also include interface to one or more communication networks. Networks can for example be wireless, wireline, optical. Networks can further be local, wide-area, metropolitan, vehicular and industrial, real-time, delay-tolerant, and so on. Examples of networks include local area networks such as Ethernet, wireless LANs, cellular networks to include GSM, 3G, 4G, 5G, LTE and the like, TV wireline or wireless wide area digital networks to include cable TV, satellite TV, and terrestrial broadcast TV, vehicular and industrial to include CANBus, and so forth. Certain networks commonly require external network interface adapters that attached to certain general-purpose data ports or peripheral buses (449) (such as, for example USB ports of the computer system 400; others are commonly integrated into the core of the computer system 400 by attachment to a system bus as described below (for example Ethernet interface into a PC computer system or cellular network interface into a smartphone computer system). Using any of these networks, computer system 400 can communicate with other entities. Such communication can be uni-directional, receive only (for example, broadcast TV), uni-directional send-only (for example CANbus to certain CANbus devices), or bi-directional, for example to other computer systems using local or wide area digital networks. Certain protocols and protocol stacks can be used on each of those networks and network interfaces as described above.

Aforementioned human interface devices, human-accessible storage devices, and network interfaces can be attached to a core 440 of the computer system 400.

The core 440 can include one or more Central Processing Units (CPU) 441, Graphics Processing Units (GPU) 442, specialized programmable processing units in the form of Field Programmable Gate Areas (FPGA) 443, hardware accelerators for certain tasks 444, and so forth. These devices, along with Read-only memory (ROM) 145, Random-access memory 446, internal mass storage such as internal non-user accessible hard drives, SSDs, and the like 447, may be connected through a system bus 448. In some computer systems, the system bus 448 can be accessible in the form of one or more physical plugs to enable extensions by additional CPUs, GPU, and the like. The peripheral devices can be attached either directly to the core's system bus 448, or through a peripheral bus 449. Architectures for a peripheral bus include PCI, USB, and the like.

CPUs 441, GPUs 442, FPGAs 443, and accelerators 444 can execute certain instructions that, in combination, can make up the aforementioned computer code. That computer code can be stored in ROM 445 or RAM 446. Transitional data can also be stored in RAM 446, whereas permanent data can be stored for example, in the internal mass storage 447. Fast storage and retrieve to any of the memory devices can be enabled through the use of cache memory, that can be closely associated with one or more CPU 441, GPU 442, mass storage 447, ROM 445, RAM 446, and the like.

The computer readable media can have computer code thereon for performing various computer-implemented operations. The media and computer code can be those specially designed and constructed for the purposes of the present disclosure, or they can be of the kind well known and available to those having skill in the computer software arts.

As an example and not by way of limitation, the computer system having architecture 400, and specifically the core 440 can provide functionality as a result of processor(s) (including CPUs, GPUs, FPGA, accelerators, and the like) executing software embodied in one or more tangible, computer-readable media. Such computer-readable media can be media associated with user-accessible mass storage as introduced above, as well as certain storage of the core 440 that are of non-transitory nature, such as core-internal mass storage 447 or ROM 445. The software implementing various embodiments of the present disclosure can be stored in such devices and executed by core 440. A computer-readable medium can include one or more memory devices or chips, according to particular needs. The software can cause the core 740 and specifically the processors therein (including CPU, GPU, FPGA, and the like) to execute particular processes or particular parts of particular processes described herein, including defining data structures stored in RAM 446 and modifying such data structures according to the processes defined by the software. In addition or as an alternative, the computer system can provide functionality as a result of logic hardwired or otherwise embodied in a circuit (for example: accelerator 444), which can operate in place of or together with software to execute particular processes or particular parts of particular processes described herein. Reference to software can encompass logic, and vice versa, where appropriate. Reference to a computer-readable media can encompass a circuit (such as an integrated circuit (IC)) storing software for execution, a circuit embodying logic for execution, or both, where appropriate. The present disclosure encompasses any suitable combination of hardware and software.

While this disclosure has described several exemplary embodiments, there are alterations, permutations, and various substitute equivalents, which fall within the scope of the disclosure. It will thus be appreciated that those skilled in the art will be able to devise numerous systems and methods which, although not explicitly shown or described herein, embody the principles of the disclosure and are thus within the spirit and scope thereof.

What is claimed is:

1. An apparatus comprising:
   at least one memory configured to store computer program code;
   at least one hardware processor configured to access said computer program code and operate as instructed by said computer program code, said computer program code including:
   obtaining code configured to cause said at least one hardware processor to obtain medical records each respectively containing at least one of different ones of a plurality of diseases and symptoms respective to the different ones of the diseases;
   sampling code configured to cause said at least one hardware processor to iteratively sample ones of candidates from a matrix of probabilistic interactions among the symptoms and the diseases that are both indicated by the medical records;
   evaluating code configured to cause said at least one hardware processor to evaluate whether a first candidate of the symptoms and diseases is more likely, than a member of Bayesian probabilities of the matrix, in a prior distribution of the first candidate under a set of the Bayesian probabilities and with respect to a first subset of the medical records, the first subset comprising all of the medical records that indicate a first of the diseases;
   replacing code configured to cause said at least one hardware processor to, in response to determining that the first candidate is more likely, than the member of the Bayesian probabilities of the matrix, in the prior distribution of the first candidate under the set of Bayesian probabilities and with respect to the first subset of the medical records, replace the member of the matrix with the first candidate and starting a next iteration, and in response to determining that the first candidate is not more likely, than the member of the Bayesian probabilities of the matrix, in the prior distribution of the first candidate under the set of Bayesian probabilities and with respect to the first subset of the medical records, replace the member with the first candidate and starting the next iteration with a different weighting.

2. The apparatus according to claim 1, wherein the computer program code is further configured to, before evaluating whether the first candidate of the symptoms and diseases is more likely than the member of the matrix, cause said at least one hardware processor to:
   generate a random variable comprising a truncated normal distribution centered at the member of the matrix from one of previous iterations; and
   draw the first candidate from the random variable.

3. The apparatus according to claim 2, wherein a variance of the random variable is adaptively changed based on the previous iterations.

4. The apparatus according to claim 1, wherein the matrix comprises an n-by-m matrix where n represents the symptoms and m represents the diseases.

5. The apparatus according to claim 1, wherein at least a plurality of the symptoms overlap between the first subset of the medical records and a second subset of the medical records, the second subset comprising all of the medical records that indicate a second of the diseases.

6. The apparatus according to claim 1, wherein the computer program code is further configured to, in the next iteration:

evaluate whether a second candidate of the symptoms and diseases is more likely, than the member of the matrix, in a prior distribution of the second candidate under the set of Bayesian probabilities and with respect to the first subset of the medical records;

in response to determining that the second candidate is more likely, than the member of the matrix, in the prior distribution of the second candidate under the set of Bayesian probabilities and with respect to the first subset of the medical records, replace the member of the matrix with the second candidate and starting a second next iteration; and in response to determining that the second candidate is not more likely, than the member of the matrix, in the prior distribution of the second candidate under the set of Bayesian probabilities and with respect to the first subset of the medical records, replace the member with the second candidate and starting the second next iteration with a second different weighting.

7. The apparatus according to claim 6, wherein the computer program code is further configured to cause said at least one processor to, before the second next iteration:
determine a first probability density function for each of a plurality of members of the matrix before the member is replaced with the first candidate;
determine a second probability density function for each of the plurality of members of the matrix after the member is replaced with the first candidate;
determine a first amount of change between the first probability density function and the second probability density function;
determine a third probability density function for each of the plurality of members of the matrix after the member is replaced with the second candidate;
determine a second amount of change between the first probability density function and the third probability density function; and
prevent the second next iteration in response to determining that a difference between the first amount of change and the second amount of change is less than a predetermined threshold.

8. The apparatus according to claim 7, wherein the computer program code is further configured to cause the at least one hardware processor to determine the first amount of change and the second amount of change by measuring Kullback-Leibler (KL) divergence.

9. The apparatus according to claim 7, wherein the computer program code is further configured to cause the at least one hardware processor to, before determining the difference and before any one of the next iteration and the second next iteration:
determine whether a user instruction has been received to halt iteratively sampling the ones of the candidates; and
prevent the one of the next iteration and the second next iteration in response to determining that the user instruction has been received.

10. The apparatus according to claim 6, wherein the computer program code is further configured to cause the at least one hardware processor to, before any one of the next iteration and the second next iteration:
determine whether a user instruction has been received to halt iteratively sampling the ones of the candidates; and
prevent the one of the next iteration and the second next iteration in response to determining that the user instruction has been received.

11. A method performed by at least one computer processor comprising:
obtaining medical records each respectively containing at least one of different ones of a plurality of diseases and symptoms respective to the different ones of the diseases;
iteratively sampling ones of candidates from a matrix of probabilistic interactions among the symptoms and the diseases that are both indicated by the medical records;
evaluating whether a first candidate of the symptoms and diseases is more likely, than a member of Bayesian probabilities of the matrix, in a prior distribution of the first candidate under a set of the Bayesian probabilities and with respect to a first subset of the medical records, the first subset comprising all of the medical records that indicate a first of the diseases;
in response to determining that the first candidate is more likely, than the member of the Bayesian probabilities of the matrix, in the prior distribution of the first candidate under the set of Bayesian probabilities and with respect to the first subset of the medical records, replacing the member of the matrix with the first candidate and starting a next iteration;
in response to determining that the first candidate is not more likely, than the member of the Bayesian probabilities of the matrix, in the prior distribution of the first candidate under the set of Bayesian probabilities and with respect to the first subset of the medical records, replacing the member with the first candidate and starting the next iteration with a different weighting.

12. The method according to claim 11, further comprising:
before evaluating whether the first candidate of the symptoms and diseases is more likely than the member of the matrix:
generating a random variable comprising a truncated normal distribution centered at the member of the matrix from one of previous iterations; and
drawing the first candidate from the random variable.

13. The method according to claim 12, wherein a variance of the random variable is adaptively changed based on the previous iterations.

14. The method according to claim 11, wherein the matrix comprises an n-by-m matrix where n represents the symptoms and m represents the diseases.

15. The method according to claim 11, wherein at least a plurality of the symptoms overlap between the first subset of the medical records and a second subset of the medical records, the second subset comprising all of the medical records that indicate a second of the diseases.

16. The method according to claim 11, further comprising in the next iteration:
evaluating whether a second candidate of the symptoms and diseases is more likely, than the member of the matrix, in a prior distribution of the second candidate under the set of Bayesian probabilities and with respect to the first subset of the medical records;
in response to determining that the second candidate is more likely, than the member of the matrix, in the prior distribution of the second candidate under the set of Bayesian probabilities and with respect to the first subset of the medical records, replacing the member of the matrix with the second candidate and starting a second next iteration; and
in response to determining that the second candidate is not more likely, than the member of the matrix, in the prior distribution of the second candidate under the set of Bayesian probabilities and with respect to the first subset of the medical records, replacing the member with the second candidate and starting the second next iteration with a second different weighting.

17. The method according to claim 16, further comprising before the second next iteration:
determining a first probability density function for each of a plurality of members of the matrix before the member is replaced with the first candidate;
determining a second probability density function for each of the plurality of members of the matrix after the member is replaced with the first candidate;
determining a first amount of change between the first probability density function and the second probability density function;
determining a third probability density function for each of the plurality of members of the matrix after the member is replaced with the second candidate;
determining a second amount of change between the first probability density function and the third probability density function; and
preventing the second next iteration in response to determining that a difference between the first amount of change and the second amount of change is less than a predetermined threshold.

18. The method according to claim 17, further comprising determining the first amount of change and the second amount of change by measuring Kullback-Leibler (KL) divergence.

19. The method according to claim 16, further comprising, before any one of the next iteration and the second next iteration:
determining whether a user instruction has been received to halt iteratively sampling the ones of the candidates; and
preventing the one of the next iteration and the second next iteration in response to determining that the user instruction has been received.

20. A non-transitory computer readable medium storing a program causing a computer to execute a process, the process comprising:
obtaining medical records each respectively containing at least one of different ones of a plurality of diseases and symptoms respective to the different ones of the diseases;
iteratively sampling ones of candidates from a matrix of probabilistic interactions among the symptoms and the diseases that are both indicated by the medical records;
evaluating whether a first candidate of the symptoms and diseases is more likely, than a member of Bayesian probabilities of the matrix, in a prior distribution of the first candidate under a set of the Bayesian probabilities and with respect to a first subset of the medical records, the first subset comprising all of the medical records that indicate a first of the diseases;
in response to determining that the first candidate is more likely, than the member of the Bayesian probabilities of the matrix, in the prior distribution of the first candidate under the set of Bayesian probabilities and with respect to the first subset of the medical records, replacing the member of the matrix with the first candidate and starting a next iteration;
in response to determining that the first candidate is not more likely, than the member of the Bayesian probabilities of the matrix, in the prior distribution of the first candidate under the set of Bayesian probabilities and with respect to the first subset of the medical records, replacing the member with the first candidate and starting the next iteration with a different weighting.

* * * * *